US010837042B2

(12) United States Patent
Baumann et al.

(10) Patent No.: US 10,837,042 B2
(45) Date of Patent: Nov. 17, 2020

(54) FEED MIXING DEVICE AND ITS USE

(71) Applicant: Hoffmann-La Roche Inc., Little Falls, NJ (US)

(72) Inventors: Sylvia Baumann, Benediktbeurn (DE); Jens Hoffmann, Penzberg (DE); Alexander Jockwer, Eurasburg (DE); Christian Klinger, Benediktbeuern (DE); Thomas Troebs, Munich (DE)

(73) Assignee: Hoffman-La Roche Inc., Little Falls, NJ (US)

( * ) Notice: Subject to any disclaimer, the term of this patent is extended or adjusted under 35 U.S.C. 154(b) by 38 days.

(21) Appl. No.: 15/713,268

(22) Filed: Sep. 22, 2017

(65) Prior Publication Data

US 2018/0010162 A1  Jan. 11, 2018

Related U.S. Application Data

(63) Continuation of application No. 13/909,591, filed on Jun. 4, 2013, now abandoned, which is a continuation of application No. PCT/EP2011/071696, filed on Dec. 5, 2011.

(30) Foreign Application Priority Data

Dec. 7, 2010 (EP) .................................... 10194025

(51) Int. Cl.
*C12P 21/00* (2006.01)
*C07K 16/24* (2006.01)
*C12M 1/34* (2006.01)
*C12N 5/00* (2006.01)
*C12M 1/00* (2006.01)
*B01F 15/04* (2006.01)

(52) U.S. Cl.
CPC .......... *C12P 21/005* (2013.01); *C07K 16/244* (2013.01); *C12M 29/26* (2013.01); *C12M 41/26* (2013.01); *C12N 5/00* (2013.01); *B01F 15/0479* (2013.01); *B01F 2215/044* (2013.01); *C07K 2317/14* (2013.01); *C12N 2500/60* (2013.01)

(58) Field of Classification Search
CPC ...... C12M 41/26; C12M 29/26; C12P 21/005; C01K 16/244; C01K 2317/14; C12N 5/00; C12N 2500/60; B01F 15/0479; B01F 2215/044
USPC ........................................................ 435/325
See application file for complete search history.

(56) References Cited

U.S. PATENT DOCUMENTS

| | | |
|---|---|---|
| 5,081,036 A | 1/1992 | Familletti |
| 5,681,748 A | 10/1997 | DiSorbo et al. |
| 5,856,179 A | 1/1999 | Chen et al. |
| 6,334,737 B1 * | 1/2002 | Lee ........................... B09B 1/00 210/170.01 |
| 6,924,124 B1 | 8/2005 | Singh |
| 7,270,751 B2 | 9/2007 | Fleury |
| 2003/0092652 A1 | 5/2003 | Bruno et al. |
| 2006/0003448 A1 | 1/2006 | Fike et al. |

FOREIGN PATENT DOCUMENTS

| | | |
|---|---|---|
| CN | 1030938 A | 2/1989 |
| CN | 101679941 A | 3/2010 |
| EA | 200702050 A1 | 4/2008 |
| EP | 0301833 A1 | 2/1989 |
| JP | 10-201467 | 8/1998 |
| JP | 2002-522468 A | 7/2002 |
| JP | 2006-513170 | 4/2006 |
| JP | 2009-165485 A | 7/2009 |
| KR | 10-2010-0077155 | 7/2010 |
| RU | 2102472 C1 | 1/1998 |
| RU | 2303572 C2 | 7/2007 |
| WO | 00/09086 A2 | 2/2000 |
| WO | 02/36735 A2 | 5/2002 |
| WO | 2004/045540 A2 | 6/2004 |
| WO | 2006/100292 A1 | 9/2006 |
| WO | 2008/013809 | 1/2008 |
| WO | 2008/109410 A1 | 9/2008 |
| WO | 2009/039657 A1 | 4/2009 |
| WO | 2009/132616 | 11/2009 |
| WO | WO-2010/034443 A2 | 1/2010 |
| WO | WO-2010/034443 A3 | 1/2010 |
| WO | 2010/045168 | 4/2010 |

(Continued)

OTHER PUBLICATIONS

Calli et al., H2 production potential in thermophilic mixed fermentation, Journal of Environmental Science and Health Part A (2009) 44, pp. 78-86.*
Aqion, pH of Common Acids and Bases, Accessed: Nov. 18, 2019, Available online at: www.aqion.de/site/191.*
Wikipedia, Magnetic stirrer, Accessed: Nov. 19, 2019, Available online at: en.wikipedia.org/wiki/Magnetic_stirrer.*
WO International Search Report of PCT/EP2011/071696; Published WO 2012/076441, pp. 1-4 ( dated Jun. 14, 2012).
Decision on Granting a Patent for Invention issued in Russian Patent Application No. 2013129008/10(043217), dated Apr. 20, 2016, with English translation (total in 13 pages).

(Continued)

*Primary Examiner* — Jennifer M. H. Tichy
(74) *Attorney, Agent, or Firm* — Morrison & Foerster LLP

(57) ABSTRACT

Herein is reported a feed mixing device for adding feed solutions with a non-physiologically pH value to a cell cultivation vessel comprising a chamber for mixing the feed solutions prior to their addition to the cell cultivation vessel as well as its use. With the feed mixing device as reported herein feed components can be provided in solution at a pH value at which they have good solubility and/or good stability whereby the pH value can be clearly different from the pH value of the cultivation medium, i.e. different from the physiological pH value. This allows performing the cultivation with more flexibility compared to a cultivation in which the pH value of the feed solution is limited to a small range around the pH value of the cultivation.

8 Claims, 20 Drawing Sheets

(56) References Cited

FOREIGN PATENT DOCUMENTS

| WO | WO-2010/045168 A1 | 4/2010 |
|----|-------------------|--------|
| WO | 2011/134919 A2    | 11/2011 |
| WO | 2011/134919 A3    | 11/2011 |
| WO | 2011/134920 A1    | 11/2011 |

OTHER PUBLICATIONS

English Abstract of WO2009/132616, pp. 1-3 ( May 31, 2013).
Office Action issued in the corresponding Chinese Patent Application No. 201180055657.2 in 7 pages, with English translation thereof (in 4 pages) (dated Jun. 5, 2014).
Bibila, T.A. et al. "Monoclonal Antibody Process Development Using Medium Concentrates," *Biotechnol. Prog.* 10(1):87-96, (Jan.-Feb. 1994).
Dempsey, J. "Improved Fermentation Processes for NS0 Cell Lines Expressing Human Antibodies and Glutamine Synthetase," *Biotechnol. Prog.* 19(1):175-178, (Jan.-Feb. 2003, e-pub. Dec. 12, 2002).
Luan Y.T. "Strategies to Extend Longevity of Hybridomas in Culture and Promote Yield of Monoclonal Antibodies," *Biotechnol. Lett.* 9(10):691-696, (Oct. 1987).
Calli et al. (2008, e-pub. Nov. 26, 2007). "Dark Fermentative H2 Production From Xylose and Lactose—Effects of On-Line pH Control," *Int. J. Hydrogen Energy* 33:522-530.

\* cited by examiner

FEED MIXING DEVICE AND ITS USE

CROSS REFERENCE TO RELATED APPLICATIONS

This application is a continuation of U.S. patent application Ser. No. 13/909,591, filed Jun. 4, 2013, which is a continuation of International Application No. PCT/EP2011/071696 having an international filing date of Dec. 5, 2011, the entire contents of each of which are incorporated herein by reference, and which claims benefit under 35 U.S.C. § 119 to European Patent Application No. 10194025.2 filed Dec. 7, 2010.

TECHNICAL FIELD

Herein is reported a feed mixing device that allows simultaneous feeding of two or more feeding solutions with non-physiological pH value to a cultivation medium whereby the pH value of the combined feed solutions is adjusted, e.g. to a physiological pH value, prior to the addition to the cultivation medium within the feed mixing device.

BACKGROUND OF THE INVENTION

To increase product yield or cultivation time in the cultivating of mammalian cells feeding solutions are added to the cultivation medium to maintain the concentration of essential medium components at or above a critical level.

Feeding of aqueous solutions with physical properties different from the cultivation medium will affect physical parameters of the cultivation medium like osmolality or pH value. Due to poor solubility or required stabilization of different components, the pH value of feeding solutions sometimes has to be changed to non-physiological values.

Luan, Y. T., et al., report strategies to extend longevity of hybridomas in culture and promote yield of monoclonal antibodies (Biotechnol. Lett. 9 (1987) 691-696). Improved fermentation processes for NS0 cell lines expressing human antibodies and glutamine synthetase is reported by Dempsey, J., et al. (Biotechnol. Prog. 19 (2003) 175-178). Bibila, T. A., et al., report monoclonal antibody process development using medium concentrates (Biotechnol. Prog. 10 (1994) 87-96).

In WO 2008/013809 cell culture methods are reported. Dry powder cells and cell culture reagents and methods of production thereof are reported in US 2006/0003448. In U.S. Pat. No. 5,081,036 a method and apparatus for cell culture is reported. Media concentrate technology is reported in U.S. Pat. No. 5,681,748. In U.S. Pat. No. 6,924,124 feeding strategies for cell culture are reported.

In WO 2009/132616 a supply system is reported. A method and apparatus for producing alcohol or sugar using a commercial-scale bioreactor is reported in WO 2010/045168. In US 2003/0092652 a protected one-vial formulation for nucleic acid molecules, methods of making the same by in-line mixing, and related products and methods are reported.

SUMMARY OF THE INVENTION

With a feed mixing device as reported herein feed components can be provided e.g. in solutions with a pH value at which the components have good solubility and/or good stability, whereby the pH value can be/is different from the pH value of the cultivation medium, i.e. different from a physiologically acceptable pH value of pH 6.5 to pH 7.5, i.e. the solutions have independently of each other a pH value of less than pH 6.5 or more than pH 7.5. This allows performing a cultivation with more flexibility compared to a cultivation in which e.g. the pH value of the feed solution is limited to a small range around the pH value of the cultivation medium.

One aspect as reported herein is a device for adding at least two solutions each with a non-physiological pH value to a cell cultivation vessel comprising a chamber for mixing the solutions prior to their addition to the cell cultivation vessel.

In one embodiment the ratio of the volume of the chamber for mixing the solutions to the volume of the cultivation medium in the cultivation vessel is of from 0.8 ml/l to 1.2 ml/l. In one embodiment the ratio is of from 0.9 ml/l to 1.1 ml/l. In one embodiment the ratio is about 1 ml/l. In one embodiment the ratio is 0.95 ml/l. In one embodiment the volume of the cultivation medium is the volume of liquid at the start of the cultivation in the cultivation vessel.

In one embodiment the at least two solutions each with a non-physiological pH value are at least one acidic solution and at least one alkaline solution. In one embodiment the at least two solutions each with a non-physiological pH value have a pH value independently of each other of less than pH 6.5 or more than pH 7.5. In one embodiment the at least two solutions each with a non-physiological pH value have a pH value independently of each of pH 0 to pH 6.49 or pH 7.51 to pH 14.

In one embodiment the pH value of the acidic and alkaline solution differs by at least 0.5 pH units from the pH value of the cultivation medium. In one embodiment the acidic solution has a pH value of pH 6.5 or lower. In one embodiment the acidic solution has a pH value of pH 4.0 or lower. In one embodiment the alkaline solution has a pH value of pH 8.0 or higher. In one embodiment the alkaline solution has a pH value of 10.0 or higher.

In one embodiment the device is for adding of from two to four separate solutions with non-physiological pH value, whereof optionally at least one is an acidic solution and at least one is an alkaline solution.

In one embodiment each of the solutions is a feed solution comprising at least one compound selected from amino acid, sugar, vitamin, trace element, lactate, and growth factor.

In one embodiment the chamber for mixing the solutions is separated from the cultivation vessel and comprises an outlet to the inside of the cultivation vessel. In one embodiment the chamber is outside of the cultivation vessel or inside the cultivation vessel.

In one embodiment the chamber has a volume of from 0.1 ml to 50,000 ml. In one embodiment the chamber has a volume of from 0.25 ml to 30,000 ml. In one embodiment the chamber has a volume of from 0.5 ml to 1,000 ml.

In one embodiment the chamber has a volume of about 1.15 ml, or about 8 ml, or about 80 ml, or about 200 ml, or about 400 ml, or about 800 ml, or about 1.6 l, or about 4 l, or about 8 l, or about 16 l, or about 40 l.

In one embodiment the mixing is immediately prior to the addition to the cultivation vessel.

In one embodiment the chamber for mixing the solutions comprises an inlet with individual connectors for each of the solutions.

In one embodiment the device is sterilizable.

Another aspect as reported herein is the use of a device as reported herein in the fed-batch or continuous cultivation of cells.

Also an aspect as reported herein is a cultivation vessel comprising a device as reported herein.

An aspect as reported herein is a method for the production of a polypeptide comprising the following steps:
cultivating a cell comprising a nucleic acid encoding the polypeptide in a fed-batch or continuous cultivation in a cultivation vessel comprising a device as reported herein whereby at least one acidic feed solution and at least one alkaline feed solution are added during the cultivating, and
recovering the polypeptide from the cultivation medium or the cells and thereby producing the polypeptide.

In one embodiment the mixed feed solutions have a pH value of from pH 4.5 to pH 9.5 upon addition to the cultivation vessel. In one embodiment the mixed feed solutions have a pH value of from pH 6.5 to pH 7.5 upon addition to the cultivation medium.

In one embodiment the cultivation vessel has a volume of about 2 l, or 10 l, or 20 l, or 100 l, or 250 l, or 500 l, or 1,000 l, or 2,000 l, or 5,000 l, or 10,000 l, or 20,000 l, or 50,000 l.

In one embodiment the volume of the cultivation medium is about 1.2 l, or about 8 l, or about 16 l, or about 80 l, or about 200 l, or about 400 l, or about 800 l, or about 1,600 l, or about 4,000 l, or about 8,000 l, or about 16,000 l, or about 40,000 l.

In one embodiment the device as reported herein is operated at room temperature.

Also an aspect as reported herein is a method for obtaining a polypeptide with a reduced G(0) glycoform and/or increased G(1) glycoform comprising the following steps:
cultivating a cell comprising a nucleic acid encoding the polypeptide in a fed-batch or continuous cultivation in a cultivation vessel comprising a device as reported herein whereby at least one acidic feed solution and at least one alkaline feed solution are added during the cultivating, and
recovering the polypeptide from the cultivation medium or the cells and thereby obtaining a polypeptide with a reduced G(0) glycoform and/or increased G(1) glycoform,
wherein the mixed feed solutions have a pH value upon addition to the cultivation vessel of from pH 4.0 to pH 6.0.

In one embodiment the polypeptide is an antibody or an Fc-fusion polypeptide.

DETAILED DESCRIPTION OF THE INVENTION

A widely used format for the production of therapeutic polypeptides or biomass is the fed-batch fermentation. Cell densities of mammalian cell cultures often exceed $100*10^5$ cells/ml in fed-batch fermentations resulting in challenges to provide sufficient amounts of the required cultivation substrates due to low solubility and/or impaired stability of certain substances or substance classes.

Therefore a common approach is to use feed solutions with non-physiological pH-values to dissolve or stabilize the required amounts of these substances. For example, an adequate supply of the amino acid tyrosine via a liquid feed solution is hardly to achieve at pH values around pH 7 due to its low solubility. Solubility however increases at high, non-physiological pH values in this case, enabling feed strategies matching overall tyrosine consumption in fed batch processes with feed solutions at non-physiological pH values. Especially continuous feeding strategies require stable feed solutions. Thus, the shelf-life of the feed components must exceed at least the feeding period.

Furthermore, addition of feed solutions with non-physiological pH values, i.e. alkaline or acidic pH values, triggers a response of the pH control mechanism of the cultivation device. This results in an increased and undesired addition of acid or base to compensate pH changes induced by the addition of feed solutions with a non-physiological pH value.

To avoid effects generated by the use of feed solutions with a non-physiological pH value, such as those with high or low pH values, a feed mixing device as reported herein can be used, enabling continuous mixing of at least two feed solutions just before addition into the cultivation vessel. By using the feed mixing device as reported herein, feed components can be dissolved at pH values at which these have good solubility and/or good stability, whereby the pH value can be clearly different from the pH value of the cultivation medium, i.e. different from a physiological pH value. This allows more flexible pH values for a feed solution, as the pH value is now adjusted directly prior to the addition to the cultivation medium and cell suspension.

The device as reported herein is a feed mixing device useful in the cultivation of cells during which compounds have to be added, such as in a fed-batch cultivation or in a continuous cultivation. With a feed mixing device as reported herein the cultivating can be performed with at least one additional degree of freedom and, thereby, with more flexibility. With the device as reported herein it is possible to use feed solutions that have a non-physiological pH value and/or a high compound concentration. The non-physiological pH value can be required e.g. for stabilizing pH-sensitive feed components. Prior to the addition to the cultivation vessel and, therewith, to the cultivation medium any pH value can be adjusted. This allows in a discontinuous or continuous feeding process to add defined amounts of compounds. For example, by the addition of defined amounts of ions a pre-defined osmolality can be adjusted.

By the gained variability of the pH value of the feed solutions that is possible by using a device as reported herein feed solutions with any pH value, i.e. alkaline, neutral or acidic solutions, and with any concentration of individual components can be used. It is also possible to exert a pH gradient in the added feed, whereby also essentially the same amount of substances can be added compared to a conventional feeding strategies not using the device as reported herein. Thus, even feed solutions can be used in which the components due to their low solubility or impaired stability have to be provided at extremely alkaline or acidic, i.e. non-physiological, pH values.

The pH value of the mixed feed solution leaving the feed mixing device and being added to the cultivation medium depends on the volumetric mixing ratio of the individual feeds and on the residence time within the mixing chamber and, therewith, on the volume flow of the individual feed solutions.

In one embodiment the total volume flow into the cultivation vessel through the feed mixing device is of from 1 to 1.5 g/h/l. In one embodiment the volume flow is of from 1.15 g/h/l to 1.35 g/h/l. In one embodiment the volume flow is about 1.25 g/h/l. The unit g/h/l denotes mass of feed/cultivation time/cultivation volume. In one embodiment the cultivation volume is the volume of liquid in the cultivation vessel at the start of the cultivation.

By using the device as reported herein for the mixing of feed solutions the viability of the cultivated cells can be maintained for a longer period of time above a pre-defined level and, therewith, allows for a longer overall cultivation time. At the same time the lactate concentration and the glucose consumption can be reduced.

The general course of the pH value of a cell cultivation is shown in FIG. 1. After inoculation (FIG. 1, "1") the pH value of the cultivation decreases and approaches the lower margin of the pre-defined pH range (FIG. 1, "2"). This is due to the formation of lactate and the accumulation of carbon dioxide in the cultivation medium. An engaged pH control mechanism ensures that the pH value is maintained at the lower margin of the pre-set pH range by the addition of base. The base addition is continued until the cell metabolism changes and the lactate in the cultivation medium is re-metabolized and/or the accumulated carbon dioxide is removed (FIG. 1, "3"). Afterwards the pH value increases until it reaches the upper margin of the pre-set pH range (FIG. 1, "4"). The pH control mechanism maintains the pH value at this upper margin value by the addition of acid.

An alkaline feed solution can maintain the pH value of the cultivation medium above the lower margin of a pre-set pH range e.g. without engagement of the pH control mechanism. Thus, the change of the pH value in the cultivation vessel can be counteracted by changing the ratio of the individual volume flow rates of the two or more feed solutions added to the cultivation medium using the feed mixing device as reported herein. Thus, with the device as reported herein a pH control mechanism or at least the time of engagement thereof (and likewise the added amounts of acid and base) might be obsolete or can be reduced, respectively.

By using an alkaline feed solution and an acidic feed solution with individual feed rates and the feed mixing device as reported herein the pH value of the combined feed solutions can be adjusted to any target value. By varying the individual feed rates and/or the feed solutions during the course of the cultivation the pH value of the combined feed solutions can be changed during the cultivation. Thus, an adaptation and/or a control of the pH value depending on the metabolism of the cultivated cells is possible. The variable pH value of the combined feed solutions can be used to support or replace other means for adjusting the cultivation pH value.

By using the feed mixing device as reported herein two or more feed solutions can be combined continuously. The feed solutions may comprise any compound. For example, compounds, such as vitamins, can be stabilized at (high) non-physiological pH values. The pH value is adjusted prior to the addition to the cultivation medium with the feed mixing device as reported herein to a pH value in the physiological range. Thus, the time at which the fed compound is kept at a stability impairing pH value is reduced.

By using one or more alkaline solutions and one or more acidic solutions a variable pH value adjustment is possible. With the device as reported herein the pH value in the cultivation medium can be controlled online by adjusting the ratio and the individual flow rates of the feed solutions (FIG. 1, "5").

By using feed solutions with different properties a time dependent adjustment of e.g. the ion concentration, the pH value, the osmolality, compound ratios, the viscosity, the surface tension, the conductivity, the wettability, the specific resistance, and/or the density is possible.

By using online sensors it is possible to combined different feed solutions with different physical and/or chemical properties with the device as reported herein. Therewith different parameters can be changed according to a pre-set schedule.

By using a device as reported herein it is possible to used solids, dispersion and hardly mixable compounds/solutions as feed solution. The chemical and/or physical properties of the feed solutions can be different.

By using a feed mixing device as reported herein a pH gradient of the added mixed feed solution during a cultivation can be performed.

The individual feeds can independently of each other be a dispersion, an emulsion, or a solution. Solutions can be transported to the feed mixing device by using conventional pumps or any other known mechanical or flow-mechanical method. If a feed is no true solution the feed can, e.g., be added by using a mechanical transportation method.

The scale of the feed mixing device is variable and, thus, the device can be used with any type and size of cultivation device, such as e.g. with a cultivation vessel (stirred tank), chip, or flow pipe reactor.

When using a device as reported herein almost no precipitate is formed in the mixing chamber although the pH value of the feed solution is profoundly changed prior to the addition to the cultivation medium upon mixing the individual feed solutions.

By using a device as reported herein and thereby adjusting the separate feeds to a combined (acidic) feed the G(0) glycoform of a produced polypeptide, especially of a produced immunoglobulin, can be reduced compared to a cultivation with a single alkaline feed and without employing the device as reported herein. Likewise the G(1) glycoform can be increased by using a device as reported herein and adjusting the separates feeds to a mixed acidic feed compared to a cultivation with a single alkaline feed and without employing the device as reported herein.

By adjusting the cell culture conditions the content of host cell protein in the cultivation medium prior to downstream processing can be changed. This should be possible by using specific feed solutions. Thus, with an adjusted feed strategy comprising pH adjusted feed solutions with a defined concentration of protons, i.e. a defined pH value, an identical or at least similar amount of feed components could be added and concurrently the amount of base or acid required in order to correct the pH value of the cultivation medium can be reduced and also concurrently the host cell protein content in the cultivation supernatant could be reduced.

Thus, the feed mixing device as reported herein is used in one embodiment for reducing the host cell protein content in a cell cultivation supernatant.

The following examples and figures are provided to aid the understanding of the present invention, the true scope of which is set forth in the appended claims. It is understood that modifications can be made in the procedures set forth without departing from the spirit of the invention.

EXAMPLES

Materials

Antibody

Figure 1:
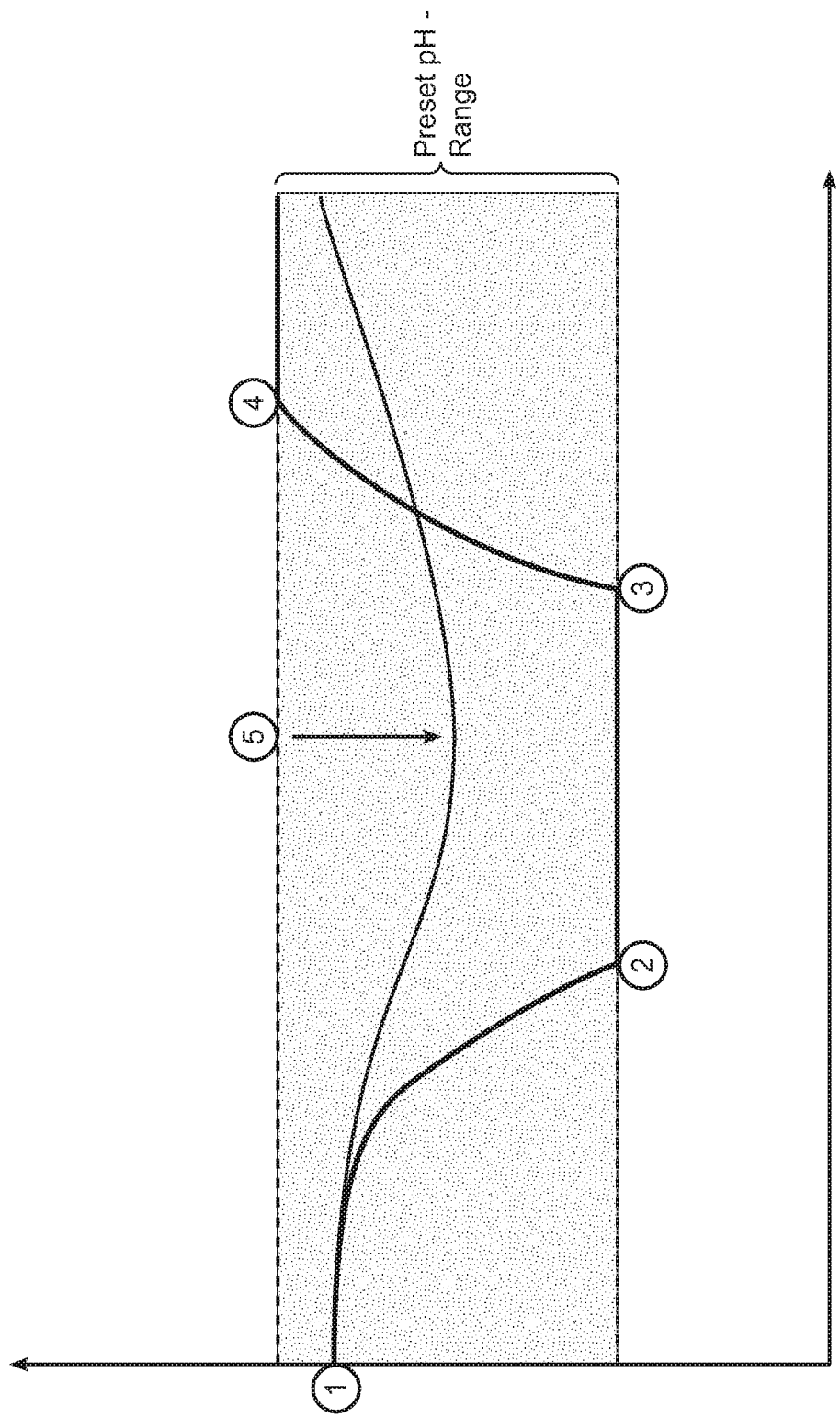
FIG. 1 Scheme of the general course of the pH value of a cell cultivation.

An exemplary antibody used in the method and examples as reported herein is an anti-IL17 antibody as reported in WO 2010/034443 (incorporated herein by reference).

Feed Solutions

Feed 1: This solution comprises all feed components (amino acids and pyruvate) at a pH value of about 9.5.

Feed 2: This solution comprises at a double concentration the components soluble at an acid pH value of about pH 1.5.
Feed 3: This solution comprises at a double concentration the components soluble at a basic pH value of about pH 10.

In this setup it is ensured that the concentration as well as the number of components as well as the volume of the added feed 1 is the same as after the combination of feed 2 and feed 3. The pH value of feed 1 is about pH 9.5 and the pH value of the combined feeds 2 and 3 is about pH 7.2.

Feed Mixing Device Dimensions

Volume of the chamber for mixing the feed solutions: 1.146 ml
Volume of the cultivation medium at the start of a cultivation with a 2 l-cultivation vessel: 1.2 l
Feed flow through the feed mixing device: 36 g/d Example 1

Four 2 l-cultivation vessels (Sartorius Biostat B-DCU Quad, Sartorius, Goettingen, Germany) have been inoculated in parallel with an inoculum solution pre-cultivated in the same shaker flask. Two cultivation vessels comprised the device as reported herein whereas the other two cultivation vessels comprised two individual conventional feeding devices with a Luer fitting but without a mixing chamber.

All cultivations were performed with a constant aeration rate, constant temperature and constant agitation speed over the entire cultivation. All feed rates are calculated based on the start working volume and are given in feed volume per fermentation starting volume per day.

The feed in the cultivation vessels comprising the feed mixing device was started after 72 hours cultivation time with feed 2 and feed 3 as continuous feed with the same volume flow. The feeds were combined in the feed mixing device and added to the cultivation medium after mixing.

The feed in the cultivation vessels comprising the conventional feeding device was started after 72 hours cultivation time with feed 1 at a volume flow twice that of the corresponding cultivations with the feed mixing device.

Thus, the added volume as well as the added amount of all feed components is identical in all four cultivations (see Tables 1 and 2).

TABLE 1

| parameter | feed solution 1 | feed solution 2 | feed solution 3 |
|---|---|---|---|
| use of device as reported herein | no | yes | yes |
| pH value | alkaline | alkaline | acidic |
| volume flow | 100% | 50% | 50% |
| concentration | 1× | 2× | 2× |
| feed rate | 0.03 1/d | 0.015 1/d | 0.015 1/d |
| total feed volume | 100% | 50% | 50% |

TABLE 2

| cultivation 1 | cultivation 2 | cultivation 3 | cultivation 4 |
|---|---|---|---|
| feed 1 +sodium chloride feed pH value 9.5 | feed 1 +potassium chloride feed pH value 9.5 | feed 2 + feed 3 +sodium chloride mixed feed pH value 7.2 | feed 2 + feed 3 +potassium chloride mixed feed pH value 7 |

Figure 2:
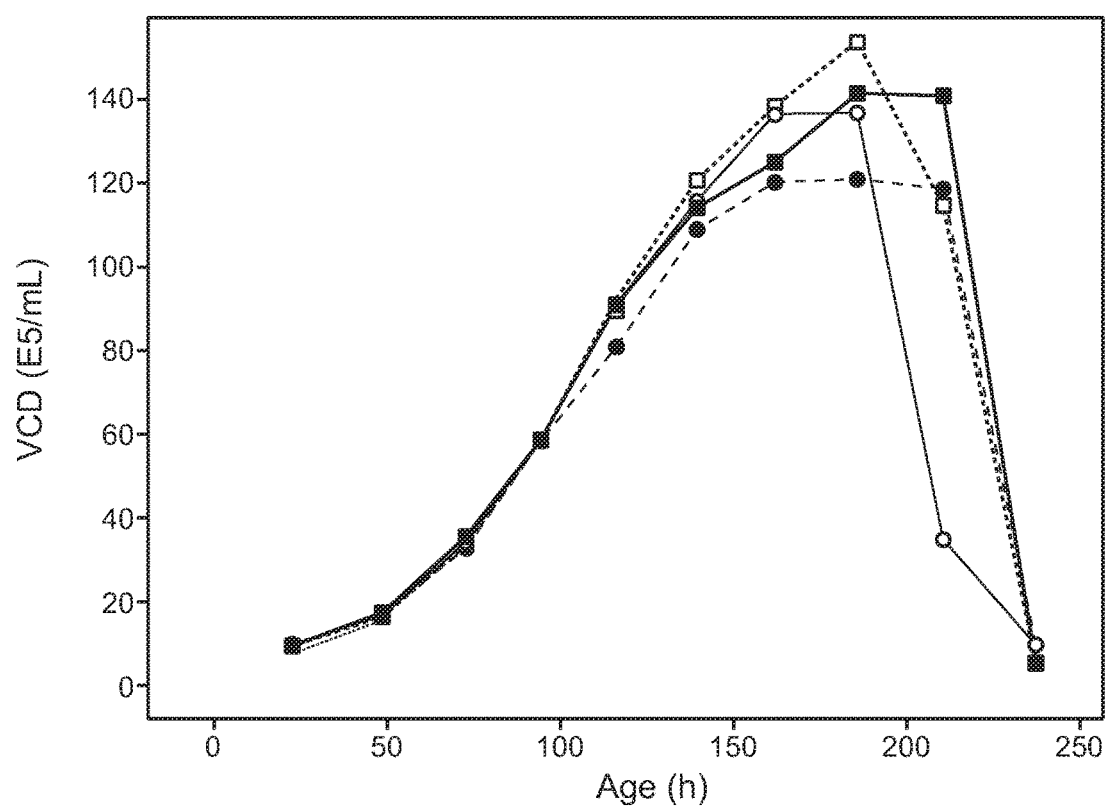
FIG. 2 Course of the viable cell density: open: single feed (feed 1); filled: separate feeds (feed 2 and feed 3); circle: with potassium chloride; square: with sodium chloride.
Figure 3:
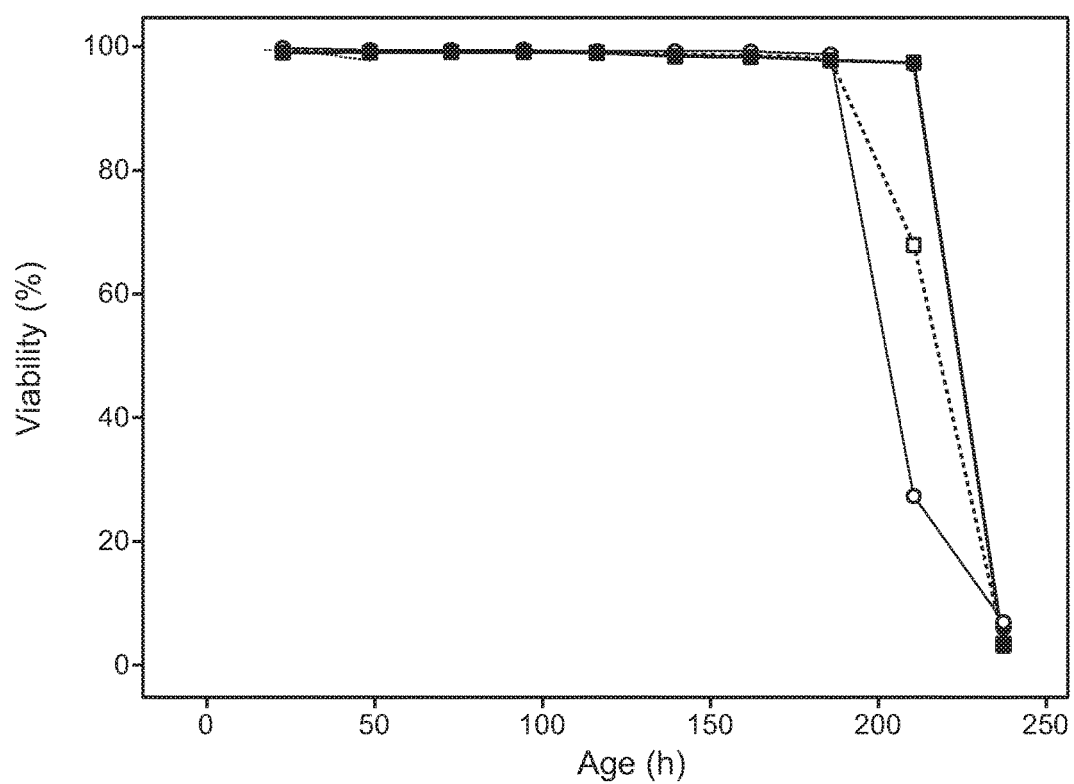
FIG. 3 Course of the viability: open: single feed (feed 1); filled: separate feeds (feed 2 and feed 3); circle: with potassium chloride; square: with sodium chloride. It can be seen that the viability by using the mixing device as reported herein remains longer at a value more than 90%.
Figure 4:
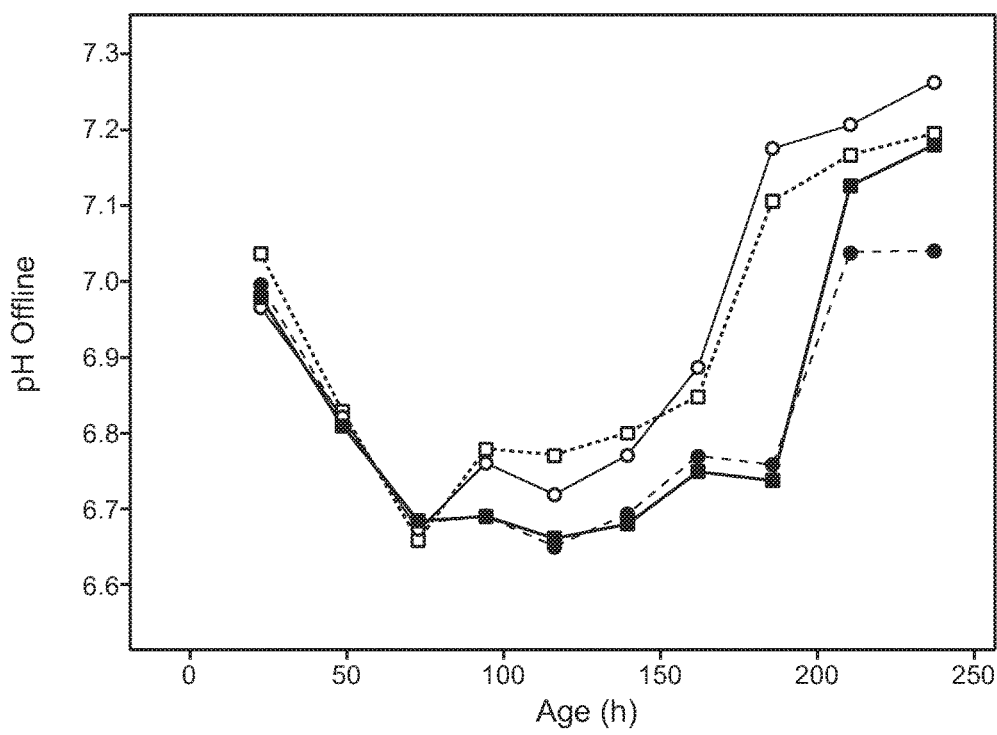
FIG. 4 Course of the pH value: open: single feed (feed 1); filled: separate feeds (feed 2 and feed 3); circle: with potassium chloride; square: with sodium chloride. Course is comparable until the start of the feeding (after 72 hours).
Figure 5:
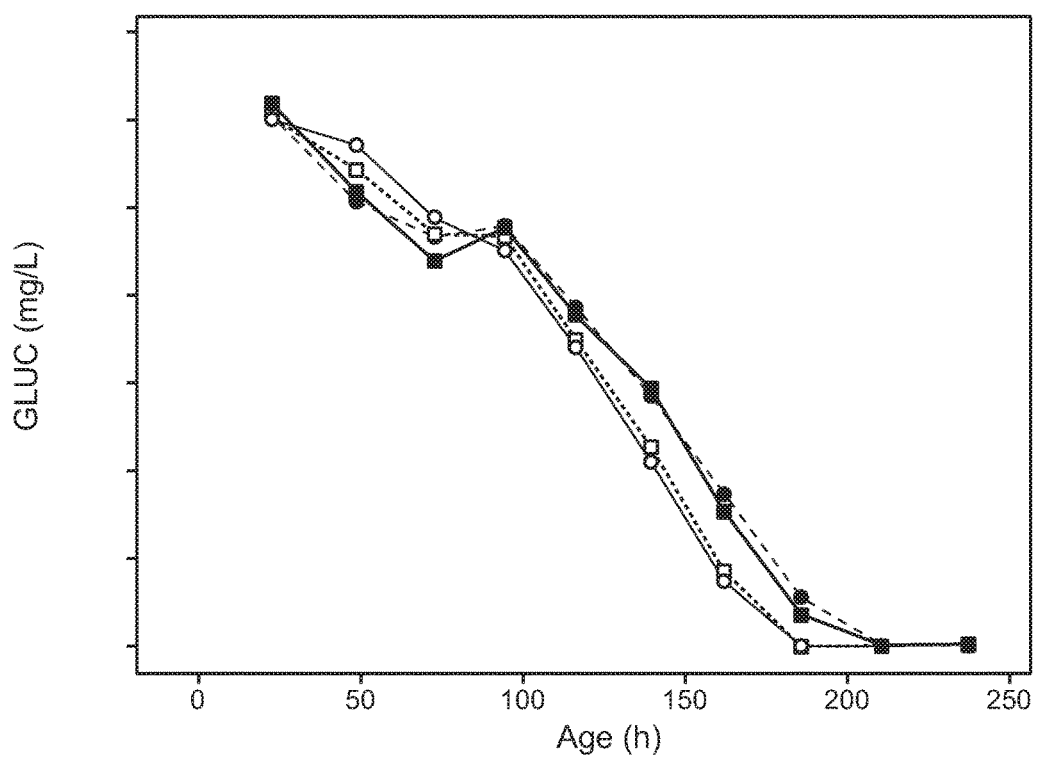
FIG. 5 Course of glucose consumption: open: single feed (feed 1); filled: separate feeds (feed 2 and feed 3); circle: with potassium chloride; square: with sodium chloride. The glucose consumption is reduced when a mixing device as reported herein is used.
Figure 6:
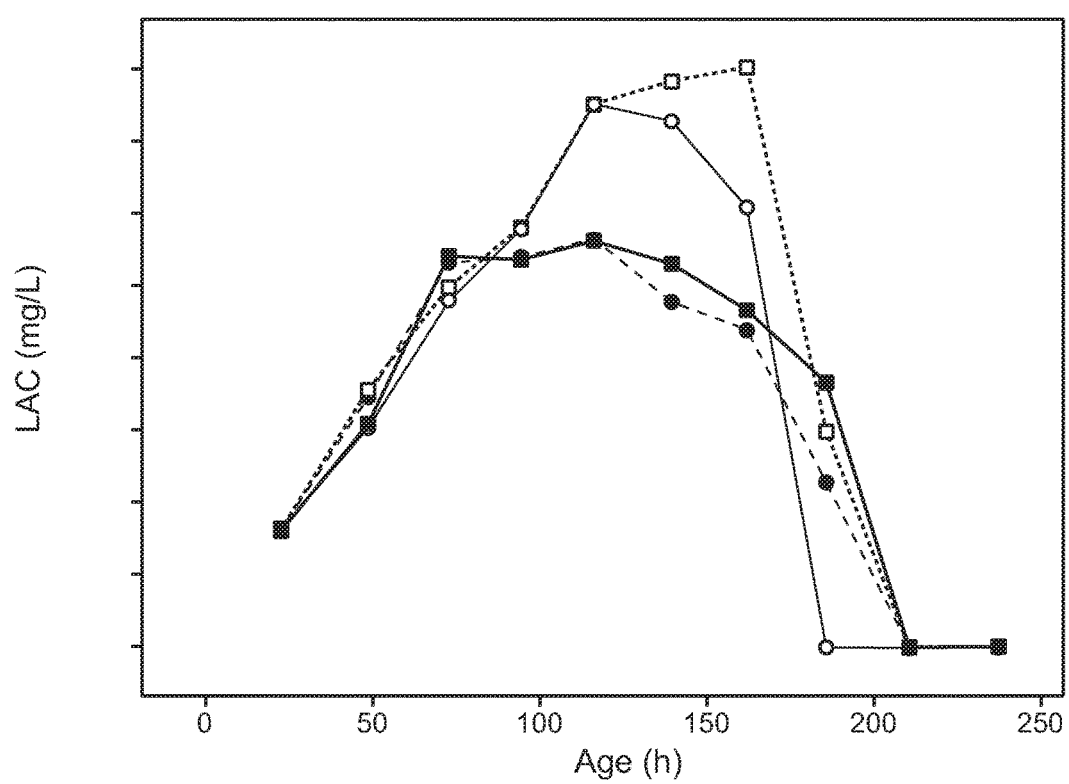
FIG. 6 Course of lactate formation: open: single feed (feed 1); filled: separate feeds (feed 2 and feed 3); circle: with potassium chloride; square: with sodium chloride. Lactate formation and onset of re-metabolism is improved upon using a mixing device as reported herein.
Figure 7:
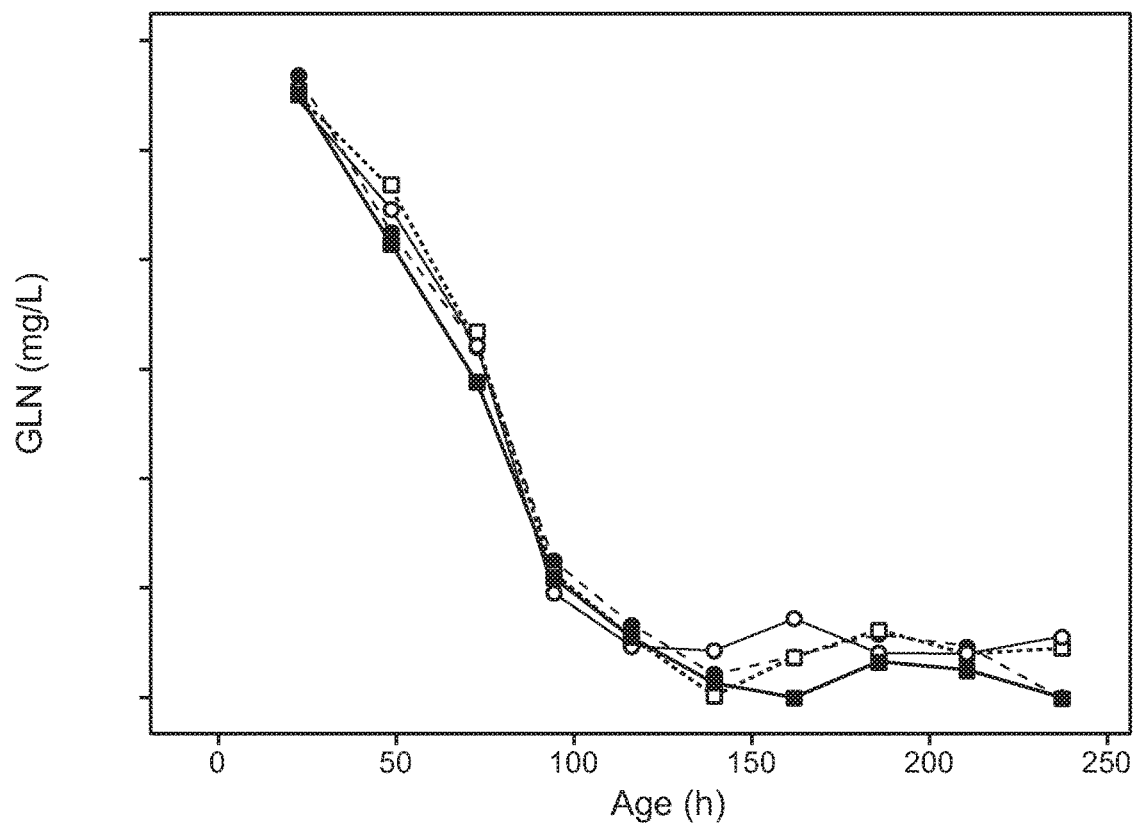
FIG. 7 Course of glutamine consumption: open: single feed (feed 1); filled: separate feeds (feed 2 and feed 3); circle: with potassium chloride; square: with sodium chloride.
Figure 8:
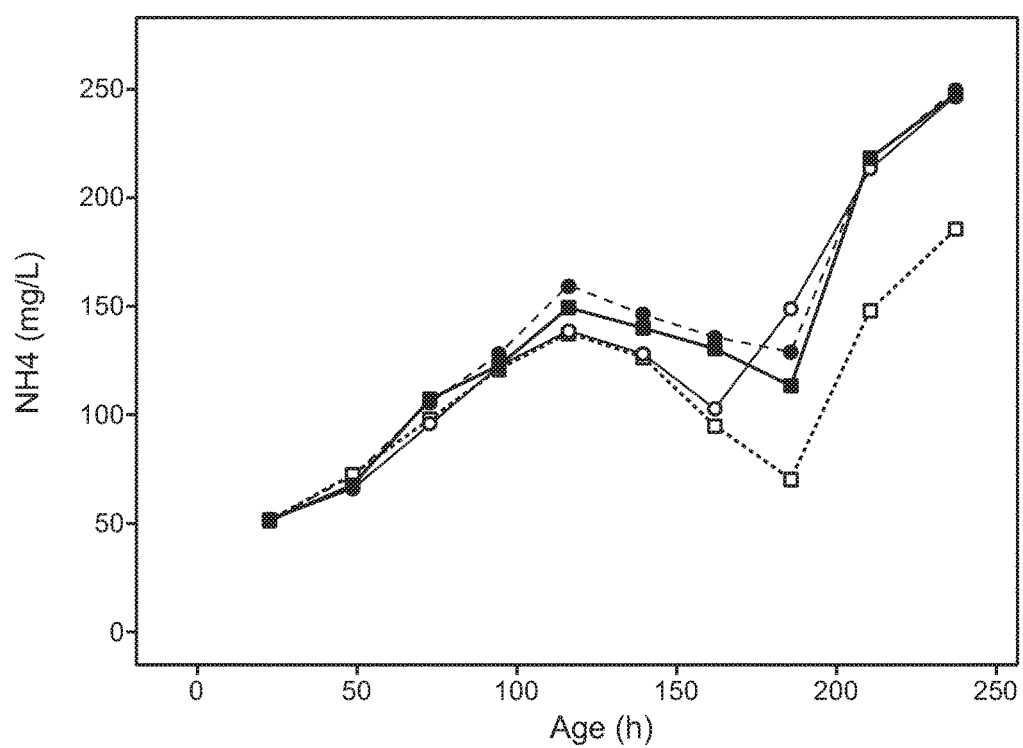
FIG. 8 Course of ammonia accumulation: open: single feed (feed 1); filled: separate feeds (feed 2 and feed 3); circle: with potassium chloride; square: with sodium chloride.
Figure 9:
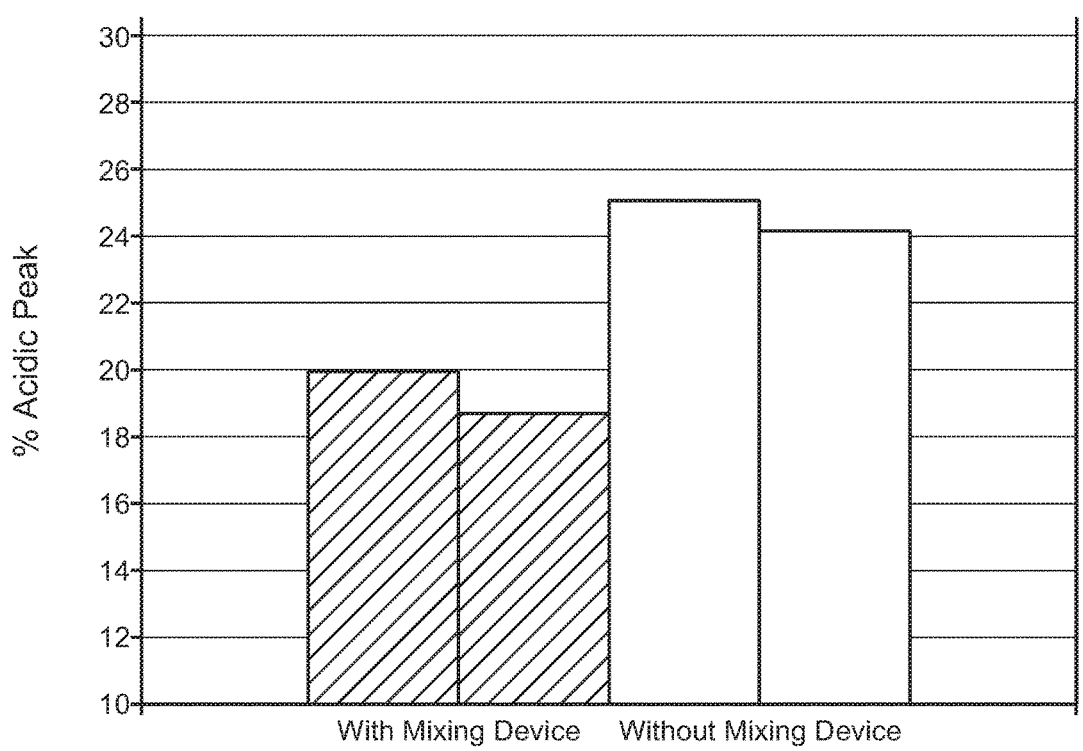
FIG. 9 Acidic peak fraction: left: use of a device as reported herein; dark right: without a device as reported herein.

The course during the cultivation of the viable cell density is shown in FIG. 2, the course of the cell viability is shown in FIG. 3, the course of the pH value in the cultivation medium is shown in FIG. 4, and the course of the glucose consumption is shown in FIG. 5. FIG. 6 shows the course of the lactate concentration during the cultivation. The course of glutamine concentration during the cultivation is shown in FIG. 7. FIG. 8 shows the course of the ammonia concentration during the cultivation. The amount of the acidic peak of the produced immunoglobulin is shown in FIG. 9.

As can be seen from the figures the viability can be maintained above 90% for an extended period of time by using the device as reported herein. The course of the pH value is comparable for the first 72 hours, i.e. prior to the start of the feeding. Thereafter the pH value of the cultivations employing the feed mixing device is below that of the other cultivations. The glucose consumption is reduced in the cultivations employing the device as reported herein. The maximum lactate concentration during the course of the cultivation with the feed mixing device is lower compared to the maximum lactate concentration of the cultivation without the feed mixing device.

Example 2

In this example only the influence of the pH value of the feed solutions on different parameters of the cultivation, such as base consumption, lactate formation, growth kinetic or product formation is analyzed. All other parameters were kept comparable.

The feed solution were composed in such a way that only the pH value after the mixing is different but all other parameters, such as the added amount of feed components, feed volume, or osmolality, are comparable. Therefore the feed solutions were not added at a constant feed rate but added by a gravimetric feeding controller.

The $pO_2$ value was adjusted to a value of 35% air saturation and determined with a $pO_2$ probe (Mettler-Toledo InPro 6820). The $pO_2$ probe was calibrated at process conditions after 72 hours of gassing in based on the mean value determined with a certified gas analytics (GA4, Dasgip). The aeration during the cultivation was kept at a constant rate of 75 ml/min of a mixture of nitrogen, air, pure oxygen and carbon dioxide. The fraction of carbon dioxide in the total gas flow was constant at 7 vol % of the total gas flow and was changed solely due to increased demand of the pH control.

The pH value of the cultivation medium was adjusted with a 1 mol/l sodium carbonate solution as base and carbon dioxide as acid to a set point of 7.0+/−0.05 pH units. The required carbon dioxide was added to the total carbon dioxide flow of 75 ml/min. The pH probe (Mettler Toledo 405-DPAS-SC-K8S/200) was calibrated with reference buffer solution of pH values 7.0 and 4.0 l and after equilibration of the cultivation medium for at least 72 hours under process conditions as mean value of a blood gas analyzer (Bioprofile, PHOx BGA).

The cultivation was performed at a constant stirrer speed of about 230 rpm. A mixer a dish stirrer was used. The power input was about 80 W/m³. The same power input was used in the pre-cultivation to ensure comparability and avoid a rapid change in the conditions.

An anti-foam solution was added based on the foam formation. No anti-foam probe was employed. The anti-foam amount required by the cultivation vessel with the highest foam formation was also added to the other cultivation vessels. As anti-foam agent 1% medical grade Dow was used.

The cultivation medium was a chemically defined medium. For each fermentation one liter of medium was used. The inoculation volume was 200 ml. Thus, the cultivation was performed with a starting volume of 1,200 ml.

As cell line a CHO cell transfected with a nucleic acid encoding an anti-IL17 antibody was used. The cell density in the 200 ml inoculation volume was adjusted to ensure a cell density of about $3.5 \times 10^5$ cells/ml in the cultivation. The power input in the inoculation cultivation was kept at the same value as the thereafter following main cultivation. The inoculation cultivation was performed at about 36.5° C., 7% $CO_2$, and a relative humidity of 85%.

After transfer of the inoculation medium to the main cultivation samples were withdrawn on a daily basis. The main cultivation was performed as a fed-batch cultivation, wherein the feeding was started approximately 72 hours after start of the main cultivation.

Five different cultivations were carried out simultaneously. The parameters thereof are given in Table 3.

TABLE 3

| parameter | cultivation 1 | cultivation 2 | cultivation 3 | cultivation 4 | cultivation 5 |
|---|---|---|---|---|---|
| use of device as reported herein | yes | yes | no | yes | yes |
| feed 1 | alkaline | alkaline | complete feed | alkaline | alkaline |
| feed 2 | acidic | acidic | — | acidic | acidic |
| pH set of feed | 9.5 | 7.0 | 9.5 | 4.5 | 4.5 |
| change of pH set of feed | no | no | no | Yes, change to pH set of 9.5 after pH value dropped to lower pH band border | no |

Results

By using feed solution the pH value of the cultivation medium is directly affected. Also affected but only indirectly is the amount of acid and/or base that has to be added during the cultivation by the pH control mechanisms.

In FIGS. 10 to 17 the influence of the pH value of the feed solution on the parameters amount of added base, amount of added acid, resulting $pCO_2$ in the cultivation medium after a cultivation time of 14 days is depicted.

Figure 10:
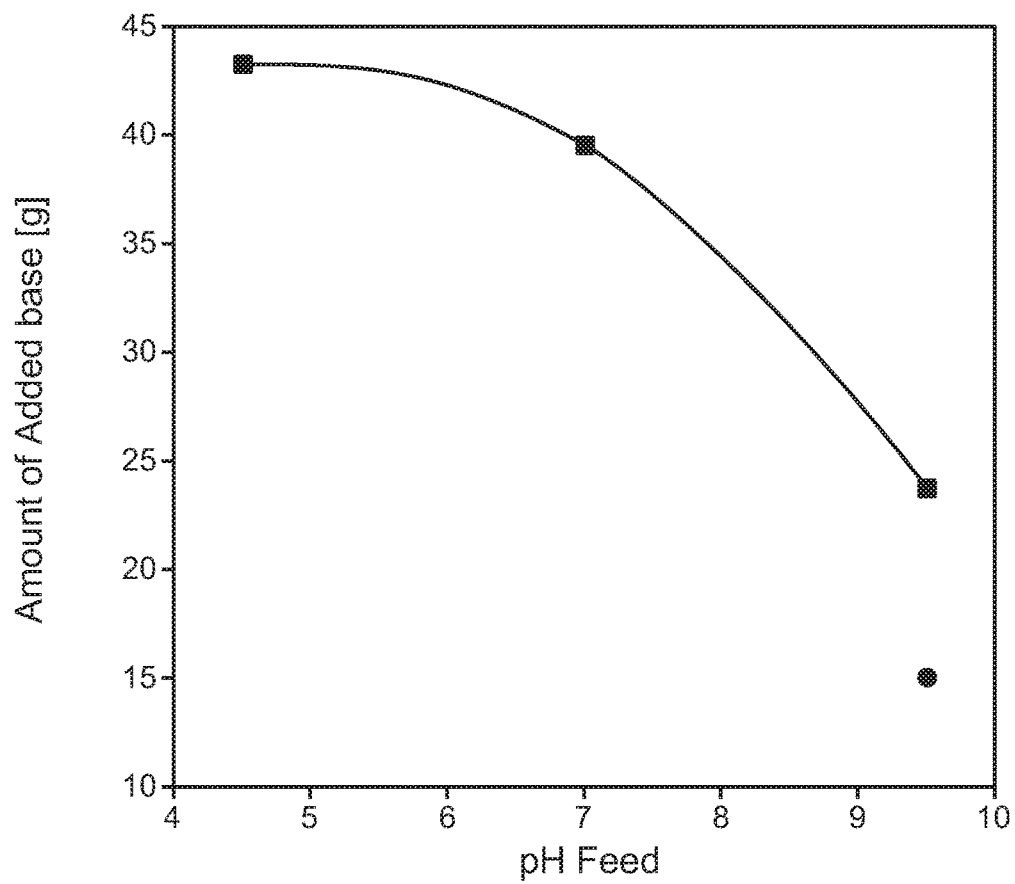
FIG. 10 Dependency of the required amount of added base (after 14 days of cultivation) on the pH value of the feed solution. Circle: without a device as reported herein; square: with a device as reported herein.

As can be seen from FIG. 10 the amount of added base is dependent on the pH value of the feed solution.

Figure 11:
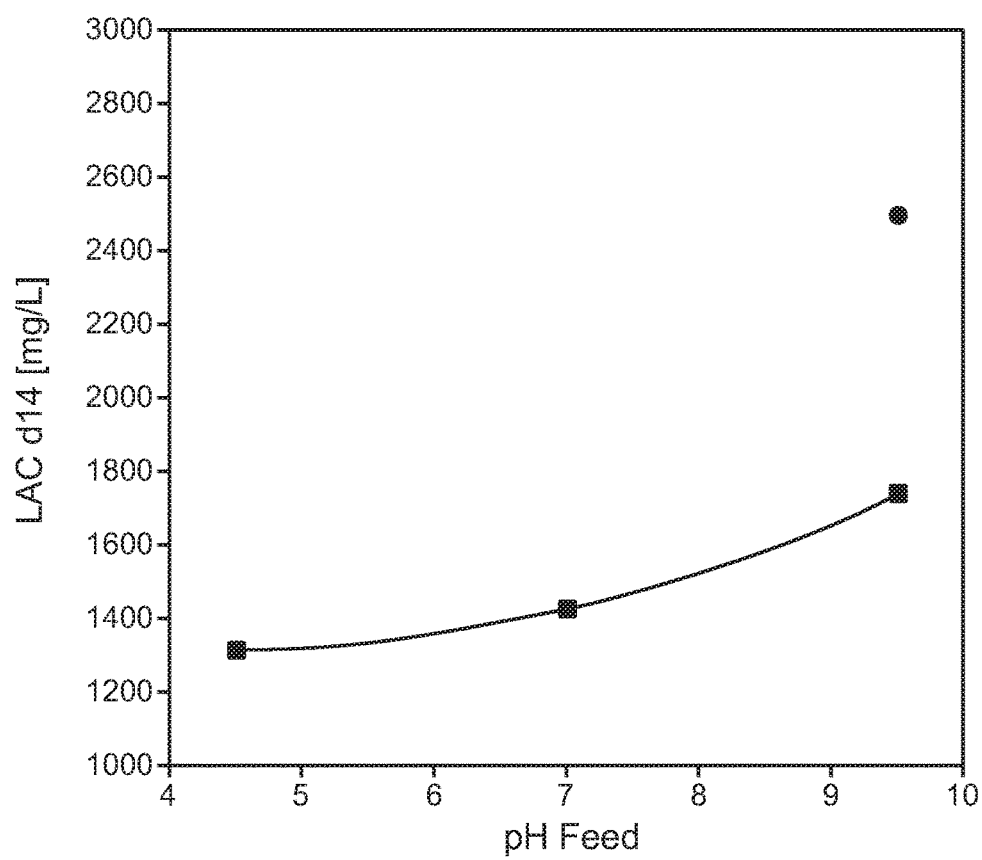
FIG. 11 Dependency of lactate formation (after 14 days of cultivation) on the pH value of the feed solution. Circle: without a device as reported herein; square: with a device as reported herein.

As can be seen from FIG. 11 the amount of lactate in the cultivation medium after a cultivation of 14 days is dependent on the pH value of the feed solution whereby the use of a feed solution of a pH value of 9.5 results in the highest amount of lactate. By using a device as reported herein the overall amount of lactate is reduced by about 30% compared to a combined feed.

Figure 12:
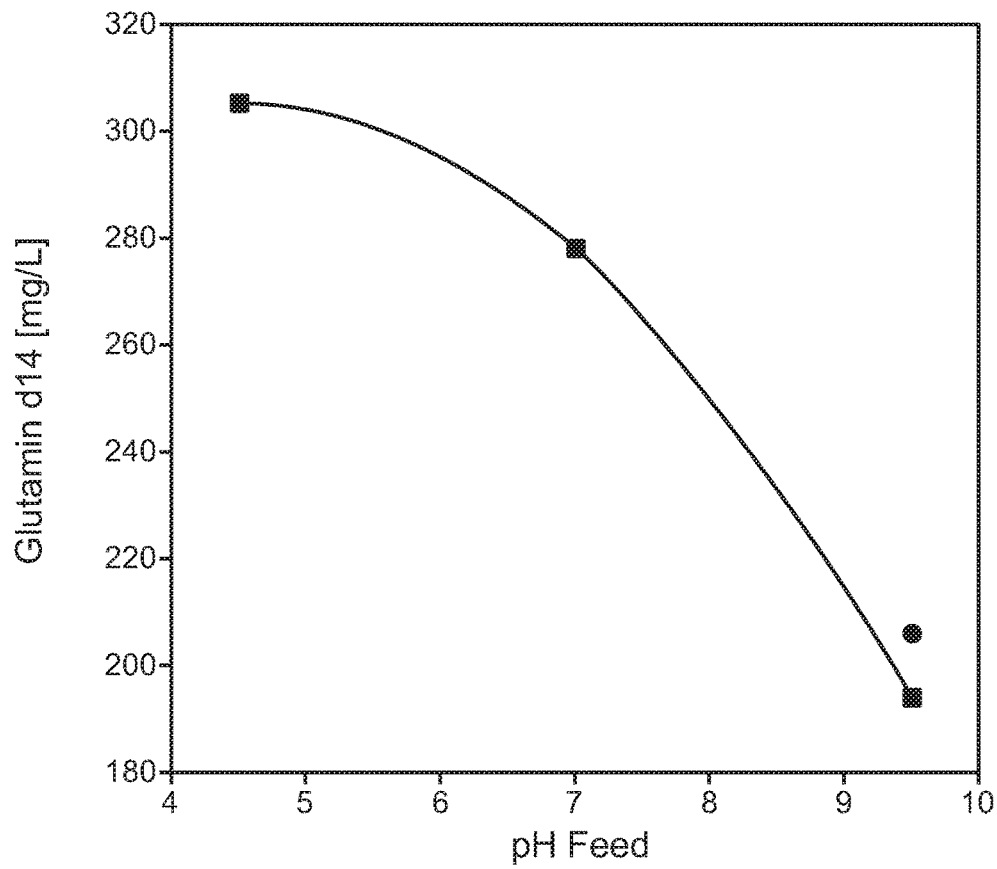
FIG. 12 Dependency of the glutamine concentration (after 14 days of cultivation) in the cultivation medium on the pH value of the feed solution. Circle: without a device as reported herein; square: with a device as reported herein.

As can be seen from FIG. 12 the amount of glutamine in the cultivation medium after a cultivation time of 14 days is dependent on the pH value of the feed solution.

Figure 13:
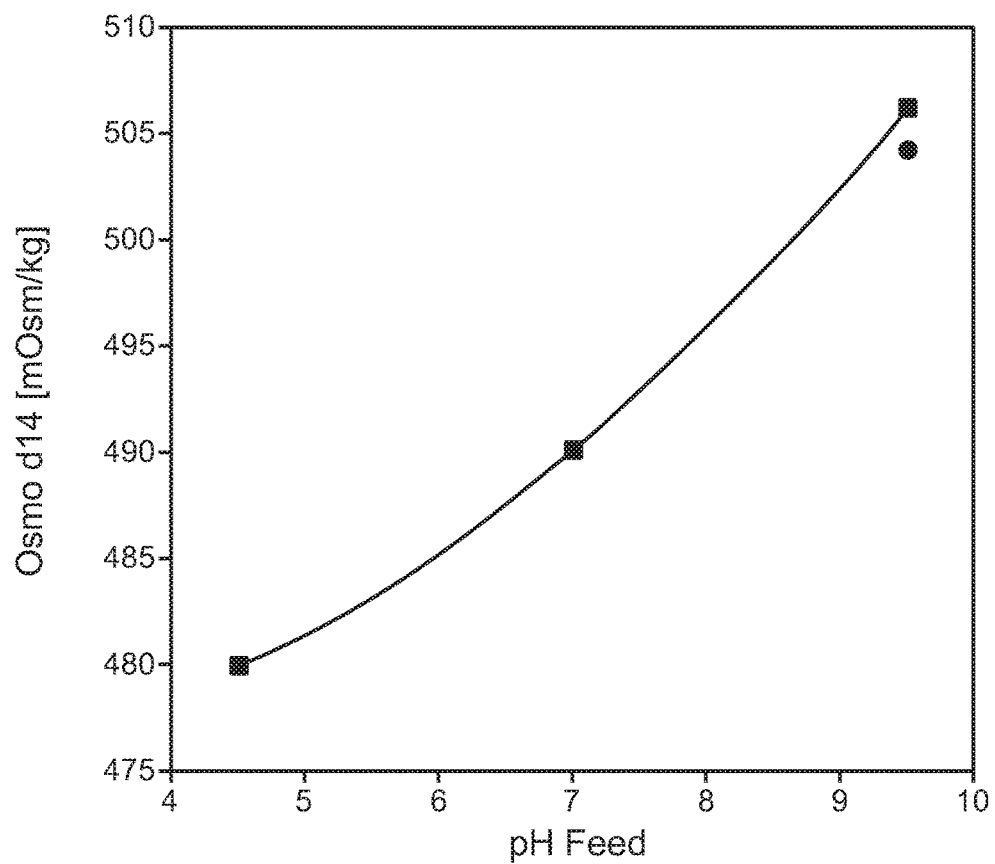
FIG. 13 Dependency of the osmolality in the cultivation medium (after 14 days of cultivation) on the pH value of the feed solution. Circle: without a device as reported herein; square: with a device as reported herein.

As can be seen from FIG. 13 the osmolality in the cultivation medium after a cultivation time of 14 days is depending on the pH value of the feed solution.

Figure 14:
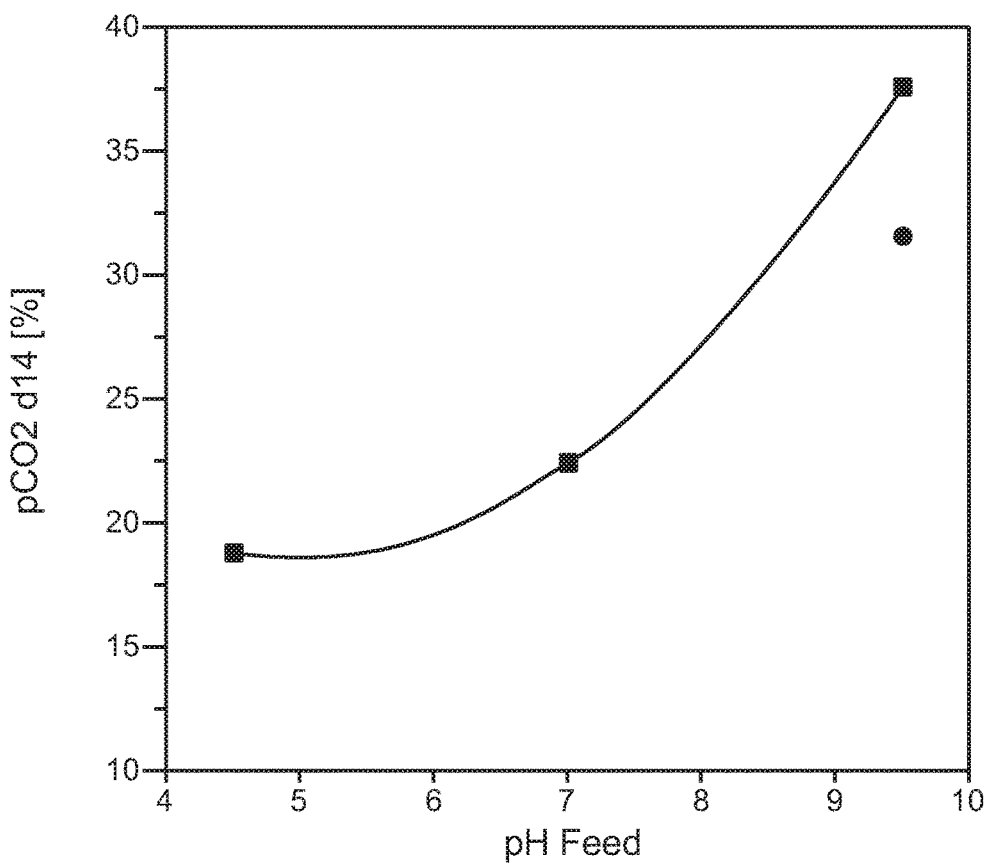
FIG. 14 Dependency of the dissolved carbon dioxide (after 14 days of cultivation) on the pH value of the feed solution. Circle: without a device as reported herein; square: with a device as reported herein.

In FIG. 14 the $pCO_2$ value in the cultivation medium after a cultivation time of 14 days is shown. It can be seen that the $pCO_2$ is dependent on the pH value of the feed solution, whereby the highest $pCO_2$ value was obtained with alkaline feed solutions, either as single feed or as mixed feed using the device as reported herein. It can be seen that by using a feed of a lower pH value the $pCO_2$ value after a cultivation time of 14 days can be dramatically reduced avoiding unphysiologically high $pCO_2$ values in the cultivation medium.

Figure 15:
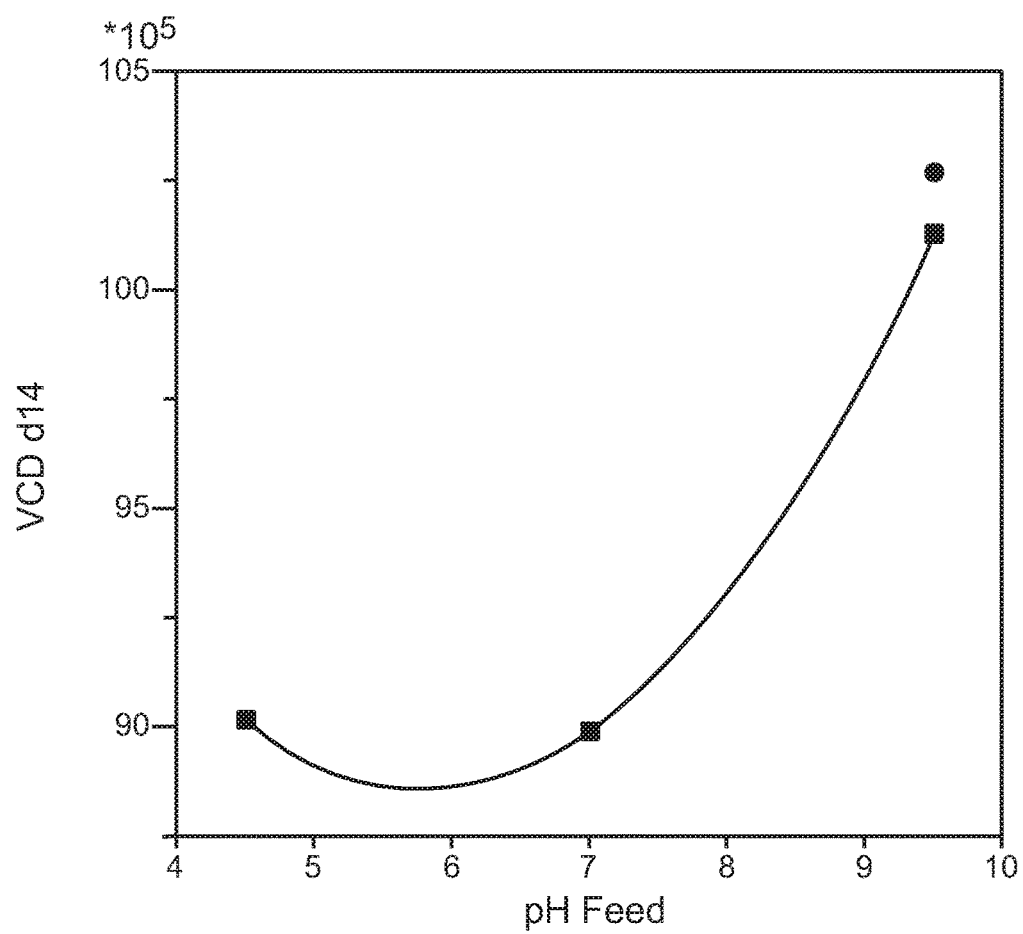
FIG. 15 Dependency of viable cell density (after 14 days of cultivation) on the pH value of the feed solution. Circle: without a device as reported herein; square: with a device as reported herein.

In FIG. 15 the viable cell density after a cultivation time of 14 days is shown. It can be seen that the viable cell density of the cultivations is at or above a value of 90%.

Figure 16:
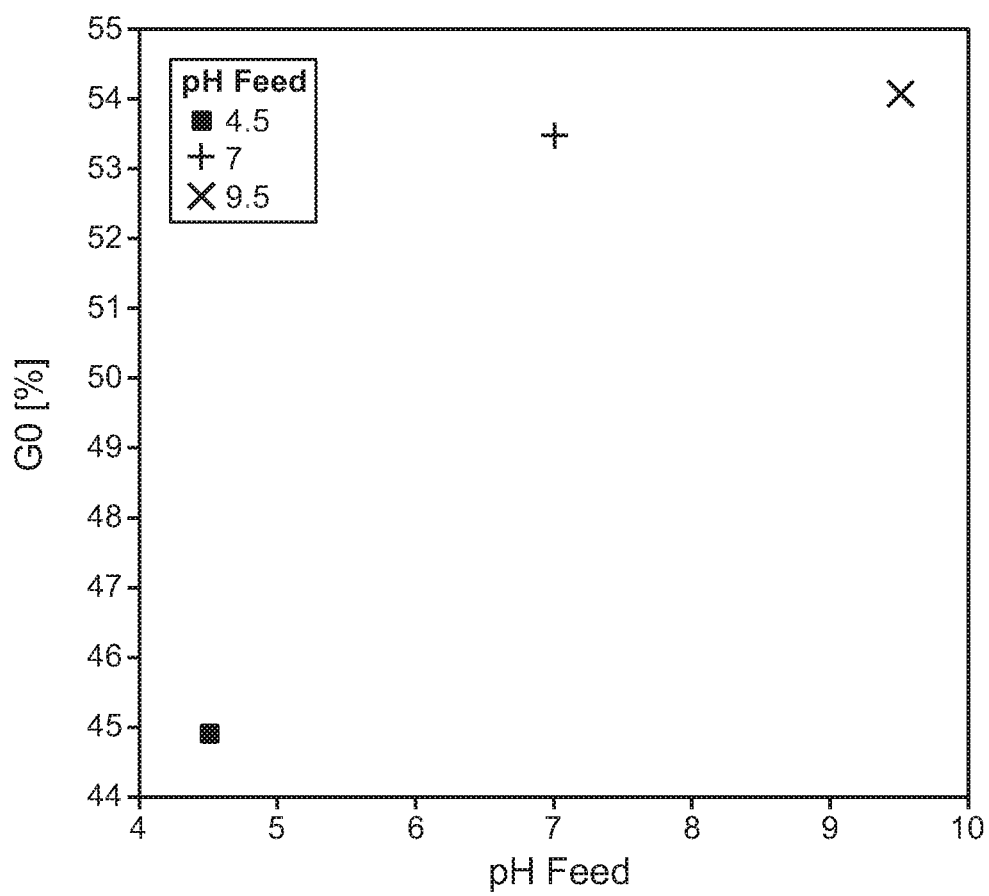
FIG. 16 Dependency of the G(0) fraction on the pH value of the feed solution.

In FIG. 16 the amount of the G(0) glycoform depending on the pH value of the feed solution is shown. It can be seen that with a neutral and an alkaline feed solution comparable amounts of the G(0) glycoform were obtained. With an acidic feed solution the amount of the G(0) glycoform was reduced.

Figure 17:
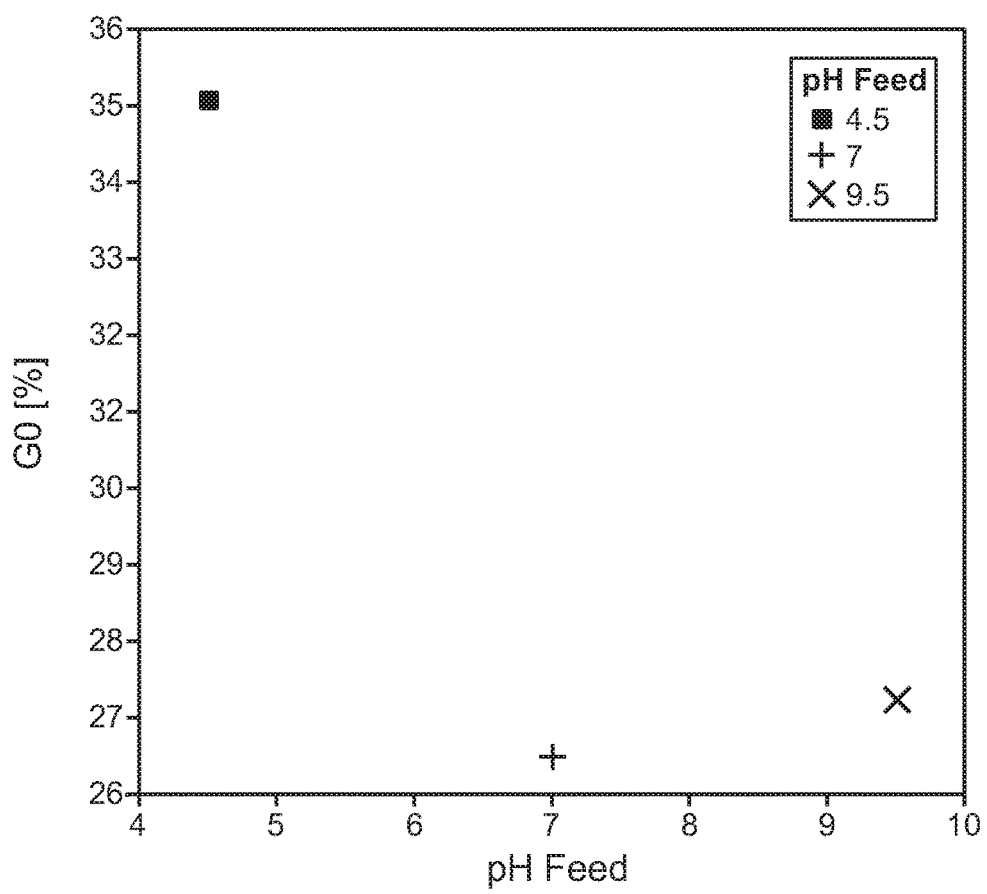
FIG. 17 Dependency of the G(1) fraction on the pH value of the feed solution.
Figure 18:
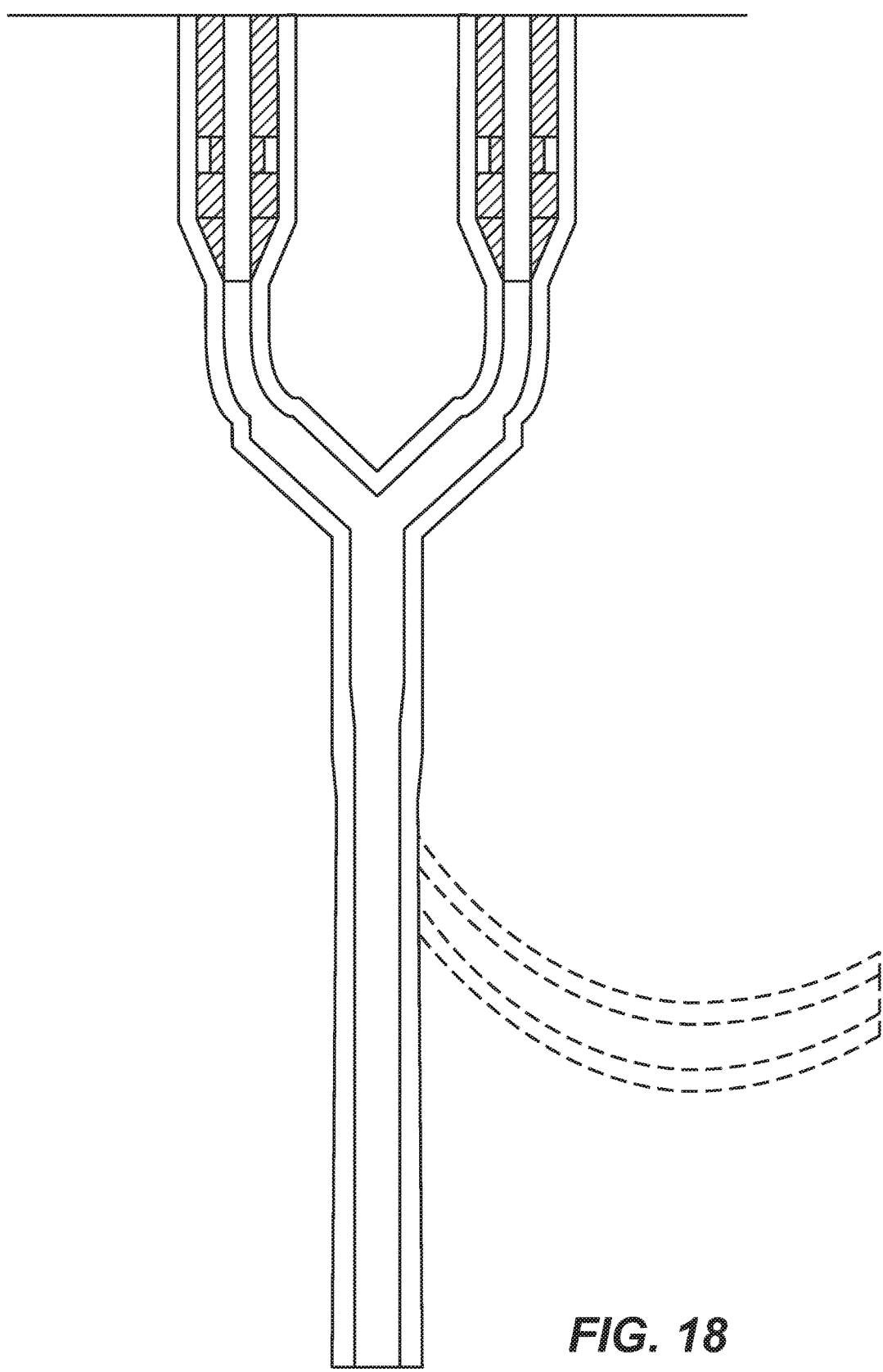
FIGS. 18+19 Exemplary schemes of the device as reported herein.
Figure 19:
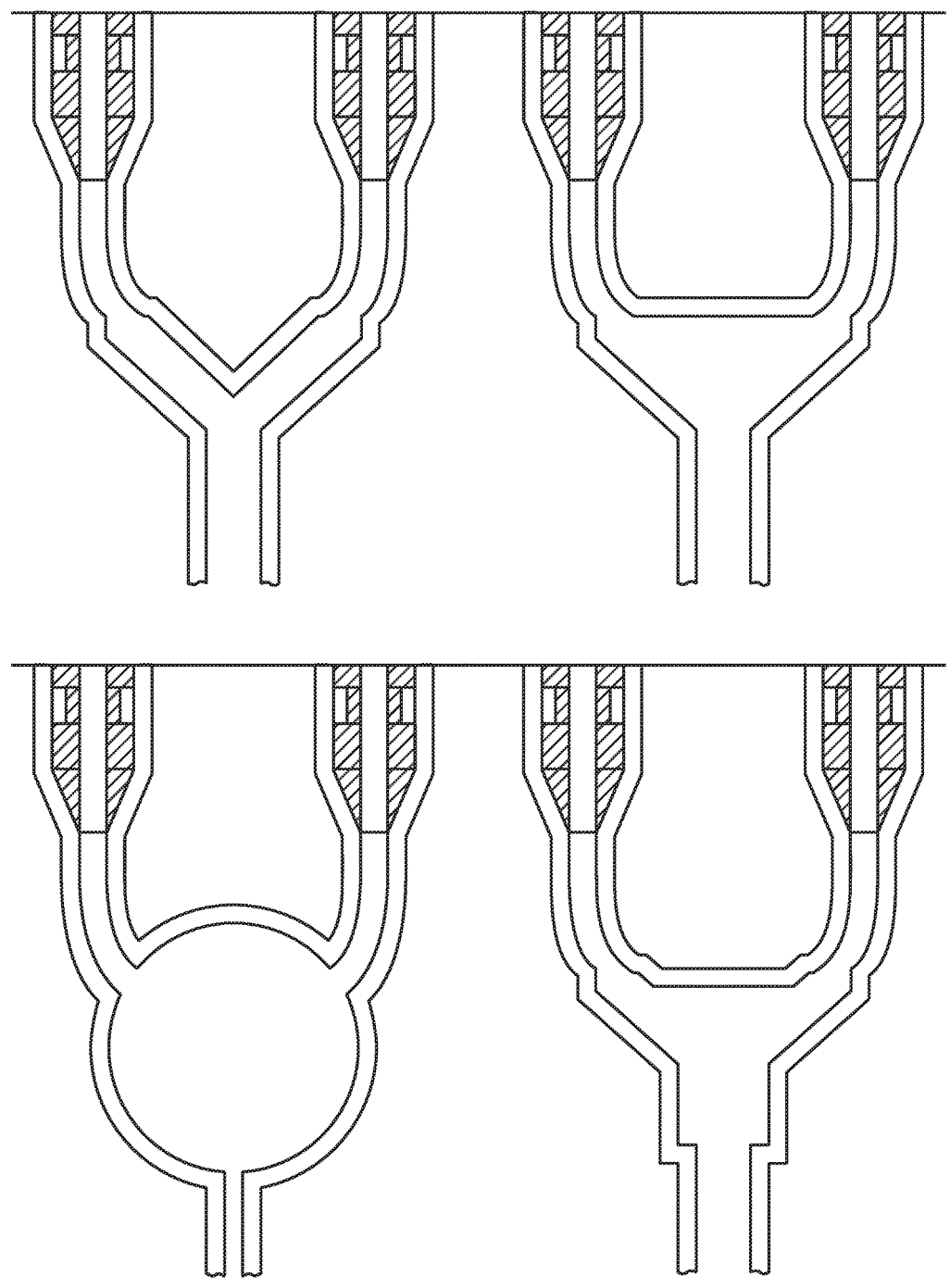
Figure 20:
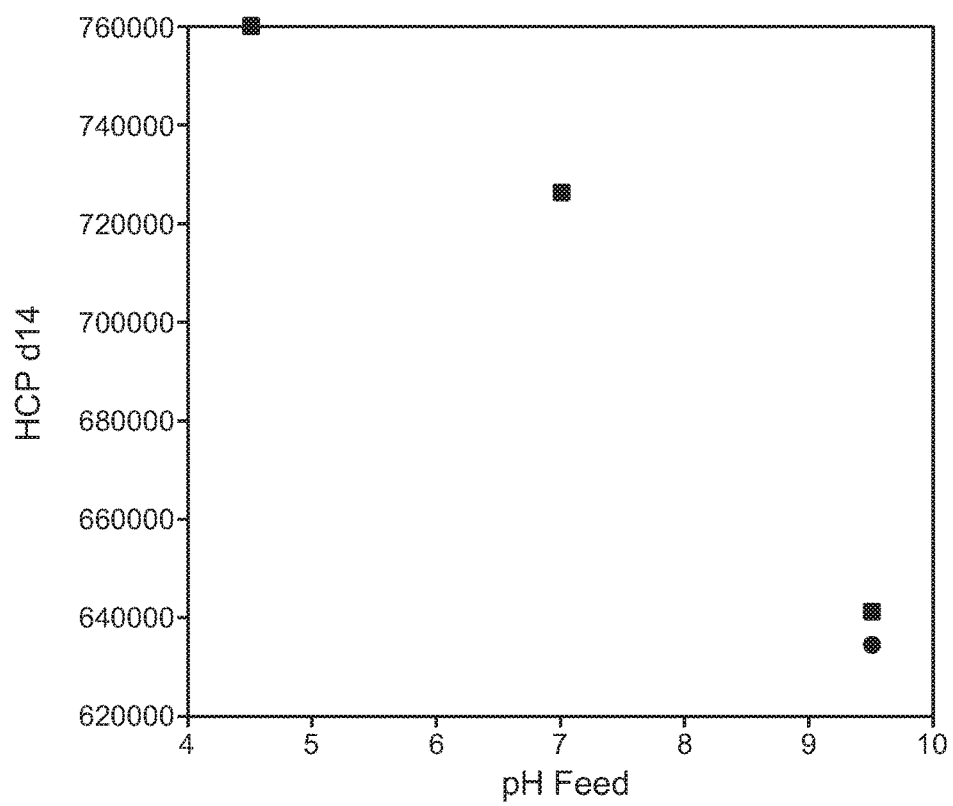
FIG. 20 Dependency of the host cell protein content on the pH value of the feed solution.

In FIG. 17 the amount of the G(1) glycoform depending on the pH value of the feed solution is shown. It can be seen that with a neutral and alkaline feed solution comparable amounts of the G(1) glycoform were obtained. With an acidic feed solution the amount of the G(1) glycoform was increased.

Example 3

Behavior of the Mixed Feeds

An alkaline feed solution of a pH value of 11.3 and an acidic feed solution of a pH value of about 1.0 were combined to obtain a target pH value of about pH 6.5. The mixing of the individual solutions was performed at room temperature and at 4° C. by combining 10 ml of each feed solution of the respective temperature.

After an incubation time of 110 min. a slight precipitate was observed for the feeds mixed and incubated at room temperature. In the feeds mixed and incubated at 4° C. a precipitate was formed already shortly after the mixing was performed.

What is claimed is:

1. A device for adding a mixed feed solution to a cell cultivation vessel comprising viable mammalian cells, the device is made of sterilizable material and comprises separate inlets for at least two feed solutions, a chamber for mixing the feed solutions to obtain the mixed feed solution, and a single outlet for directly adding the mixed feed solution to the cell cultivation vessel, whereby at least one feed solution is an acidic feed solution and has a pH value of less than pH 6.5, and at least one feed solution is an alkaline feed solution and has a pH value of more than pH 7.5, the chamber for mixing the feed solutions has a volume of from 0.8 ml to 1.2 ml per liter of cultivation medium in the cultivation vessel.

2. The device according to claim 1, characterized in that the volume of the chamber is from 0.9 ml to 1.1 ml per liter of the cultivation medium.

3. The device according to claim 1, characterized in that the chamber is outside of the cultivation vessel and the outlet is inside of the cultivation vessel.

4. The device according to claim 1, characterized in that the chamber and the outlet are inside the cultivation vessel.

5. The device according to claim 1, characterized in that the chamber for mixing the feed solutions has a volume of from 0.5 ml to 1,000 ml.

6. The device of claim 1, characterized in that the chamber for mixing the feed solutions has a volume of about 1.15 ml.

7. The device of claim 1, characterized in that the device further comprises a first liquid storage unit containing the acidic feed solution and a second liquid storage unit containing the alkaline feed solution.

8. The device of claim 7, characterized in that each of the alkaline and acidic feed solutions comprises at least a compound selected from amino acid, sugar, vitamin, trace element, lactate, and growth factor.

* * * * *